United States Patent
Hermann et al.

(10) Patent No.: US 10,286,114 B2
(45) Date of Patent: May 14, 2019

(54) DEVICE AND METHOD FOR TARGETED RADIATION THERAPY

(71) Applicant: Focal Therapeutics, Inc., Portola Valley, CA (US)

(72) Inventors: George D. Hermann, Portola Valley, CA (US); Gail S. Lebovic, Frisco, TX (US)

(73) Assignee: FOCAL THERAPEUTICS, INC., Portola Valley, CA (US)

( * ) Notice: Subject to any disclaimer, the term of this patent is extended or adjusted under 35 U.S.C. 154(b) by 184 days.

(21) Appl. No.: 13/802,041

(22) Filed: Mar. 13, 2013

(65) Prior Publication Data
US 2014/0275984 A1    Sep. 18, 2014

(51) Int. Cl.
| | |
|---|---|
| *A61L 29/02* | (2006.01) |
| *A61M 25/01* | (2006.01) |
| *A61M 27/00* | (2006.01) |
| *A61L 29/18* | (2006.01) |

(52) U.S. Cl.
CPC .............. *A61L 29/02* (2013.01); *A61L 29/18* (2013.01); *A61M 25/0102* (2013.01); *A61M 27/008* (2013.01); *A61L 2400/16* (2013.01)

(58) Field of Classification Search
CPC ... A61M 27/00; A61M 25/0102; A61L 29/02; A61L 29/18; A61L 2400/16; A61B 19/54
See application file for complete search history.

(56) References Cited

U.S. PATENT DOCUMENTS

| | | |
|---|---|---|
| 4,957,479 A | 9/1990 | Roemer |
| 5,873,865 A | 2/1999 | Horzewski et al. |
| 2001/0047164 A1 | 11/2001 | Teague et al. |
| 2005/0143770 A1* | 6/2005 | Carter ............... A61B 1/018 606/170 |
| 2007/0219446 A1* | 9/2007 | Beyhan ............... A61B 8/12 600/439 |
| 2008/0015472 A1 | 1/2008 | Ressemann et al. |
| 2008/0045773 A1* | 2/2008 | Popowski ........... A61N 5/1015 600/4 |
| 2008/0288068 A1* | 11/2008 | Kronowitz ............ A61F 2/12 623/8 |
| 2009/0318898 A1* | 12/2009 | Dein ................. A61M 27/00 604/541 |
| 2012/0059285 A1 | 3/2012 | Soltani et al. |

FOREIGN PATENT DOCUMENTS

WO    WO-2014/059041 A1    4/2014

OTHER PUBLICATIONS

International Search Report dated Mar. 10, 2014 for PCT Patent Application No. PCT/US13/64168, filed on Oct. 9, 2013, 4 pages.
Written Opinion dated Mar. 10, 2014 for PCT Patent Application No. PCT/US13/64168, filed on Oct. 9, 2013, 6 pages.

* cited by examiner

*Primary Examiner* — Bo Joseph Peng

(57) ABSTRACT

Described here are temporary devices for placement into tissue cavities at the time of a surgical procedure. In addition to marking the tissue cavity for radiation therapy, the devices are capable of draining fluid from the cavity. The devices generally include a resilient, volumetrically shaped distal portion. The shape of the distal portion may be released when removal of the device from the tissue cavity is desired.

7 Claims, 5 Drawing Sheets

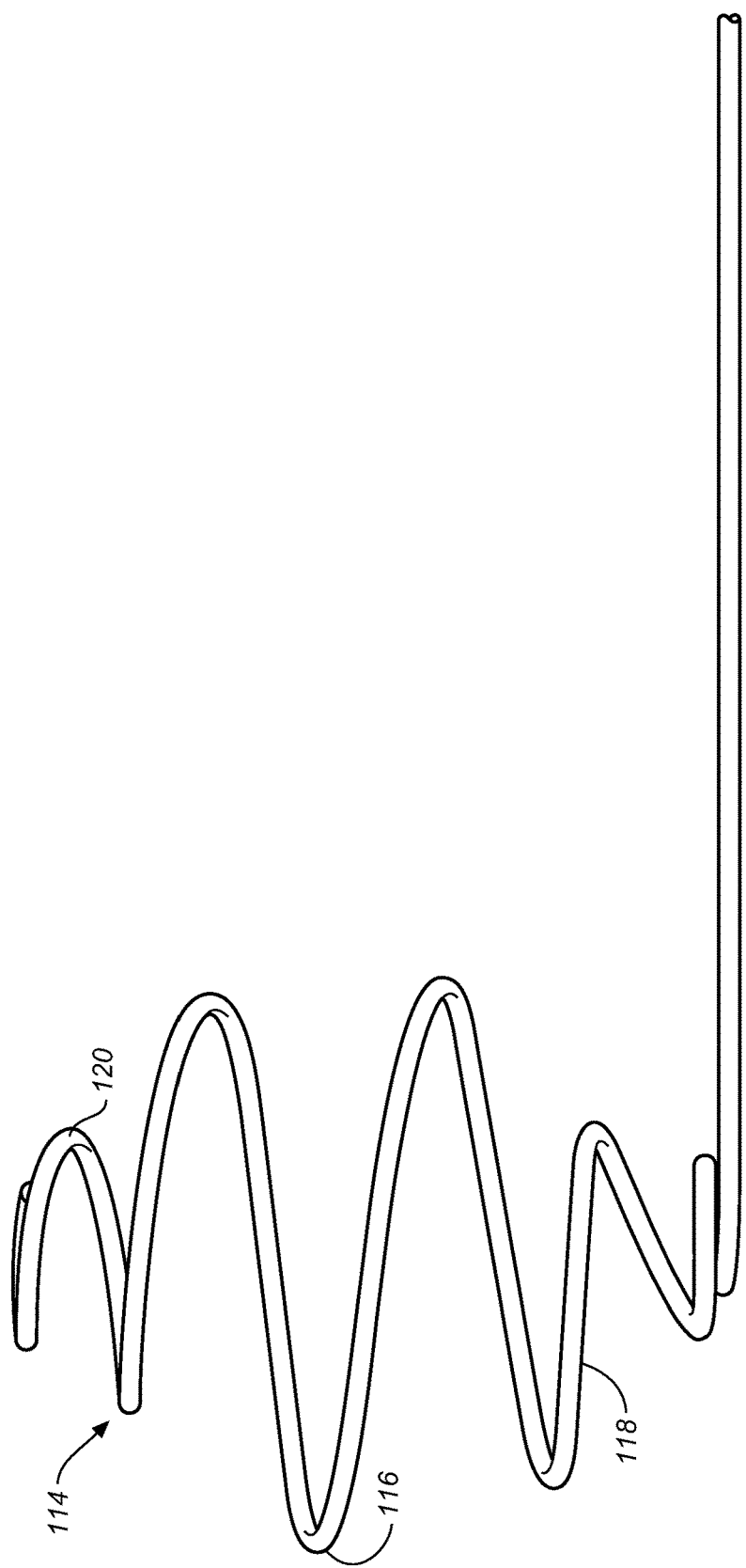

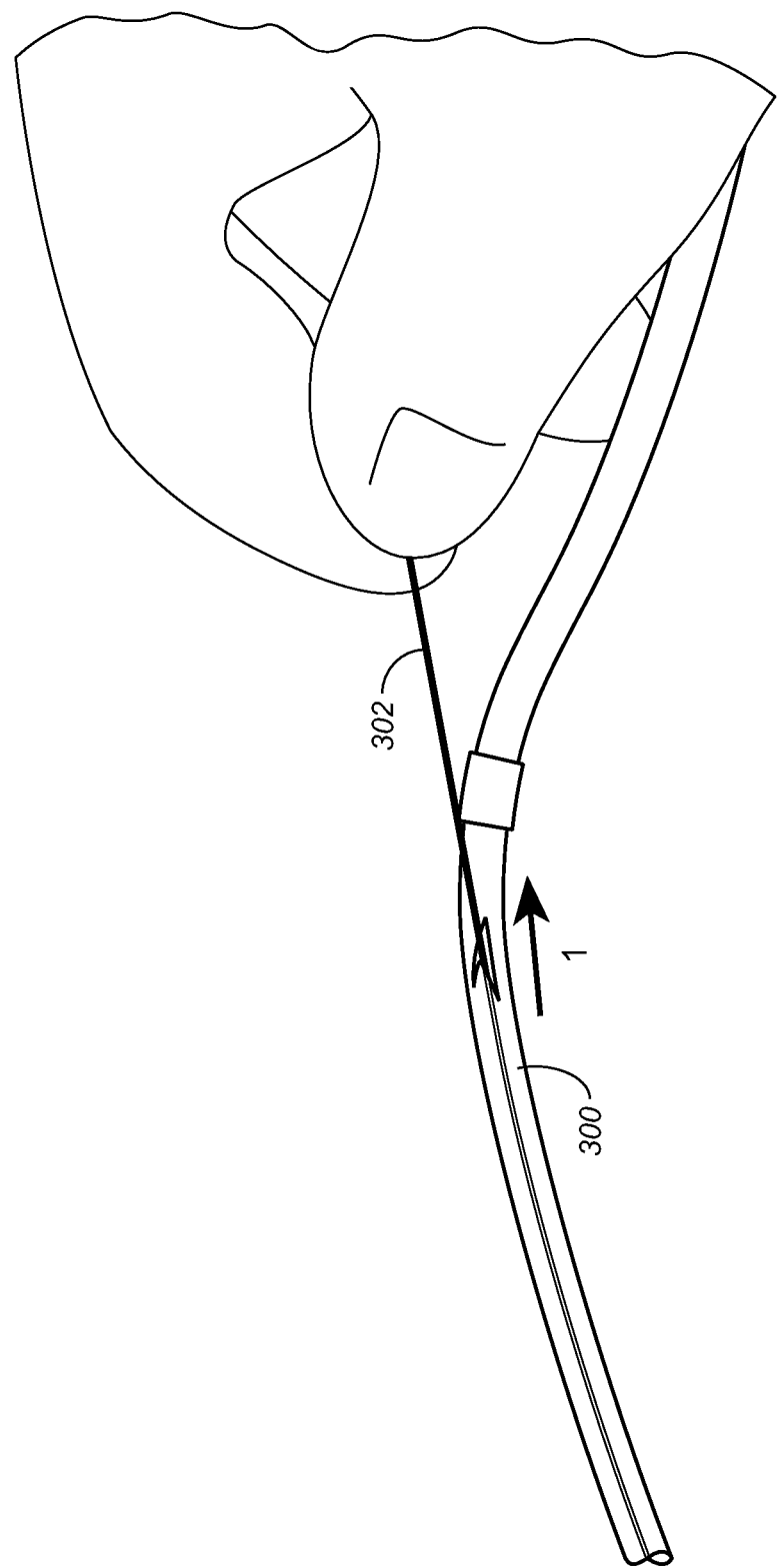

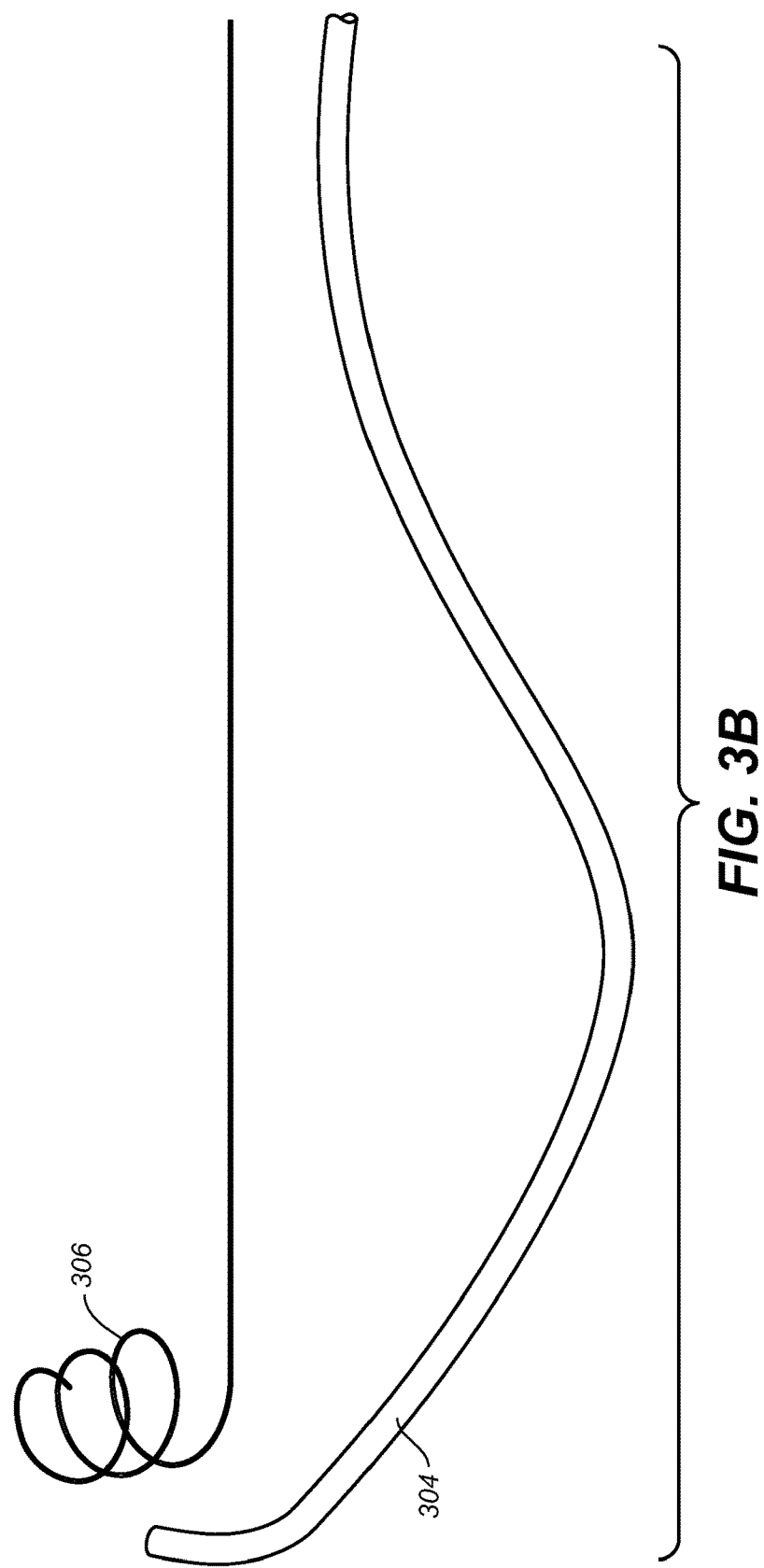

DEVICE AND METHOD FOR TARGETED RADIATION THERAPY

CROSS-REFERENCE TO RELATED APPLICATIONS

This application claims priority to U.S. Provisional Application Ser. No. 61/711,606 filed Oct. 9, 2012, which is hereby incorporated by reference in its entirety.

FIELD

Described here are temporary devices for placement into tissue cavities at the time of a surgical procedure. In addition to marking the tissue cavity for radiation therapy, the devices are capable of draining fluid from the cavity. Related methods are also described.

BACKGROUND

External beam radiation therapy (EBRT) is a commonly used method of treating many different types of cancers, including breast cancer. Implementation of EBRT generally involves generation of high energy x-ray beams by a linear accelerator, and delivery of those beams to a patient's tumor or target tissue site. With careful treatment planning, the goal of EBRT is to deposit the high energy x-rays in the area of the cancer (e.g., the tumor mass itself, or tissue margin thereof after resection) to destroy cancer cells, while minimizing damage to normal, surrounding tissues. EBRT may be performed before or after surgery to remove a cancerous tumor, to reduce tumor size prior to surgery, or to prevent the cancer from recurring after surgery.

The treatment planning process will typically include the use of a specialized computer to calculate the radiation dose that will be delivered to the patient's target site and surrounding normal tissue. As part of the process, the volume of the tumor or other areas that require treatment are determined and outlined on treatment planning images (e.g., from CT, MRI, ultrasound, and/or PET/CT images). Normal structures that should be avoided or considered in devising treatment may also be outlined. Using that information, a treatment plan that delivers an appropriate radiation dose while minimizing dose to surrounding normal tissues can be generated. In certain instances, the process may employ such techniques as three-dimensional conformal radiation therapy or intensity-modulated radiation therapy.

Fiducial markers are widely used in image-guided radiation therapies such as external beam radiation therapy to more accurately localize the area to be irradiated. The fiducial markers generally have different radiographic properties than that of the surrounding tissue, e.g., soft tissue, bone, etc., and thus can help to distinguish between the tissues when imaged. The fiducials may be implanted into tissue, into resection cavities (e.g., a lumpectomy cavity), or both. After a lumpectomy, it is not uncommon for a clear fluid ("seroma") to build up in the space previously occupied by breast tissue and also in other regions of the breast. Due to tissue changes as a result of the surgery, the presence of seroma fluid on radiographic images often makes it difficult to accurately determine the volume of tissue needing treatment. Thus, to avoid undertreating the area, the treatment volume is generally overestimated, which subsequently leads to radiation damage of a larger amount of normal tissue.

Accordingly, it would be useful to have fiducial devices with improved marking capabilities. Specifically, improved devices and methods for marking surgically formed cavities would be beneficial. Fiducial devices being capable of temporary placement within these tissue cavities, and related methods, would also be beneficial.

SUMMARY

Described herein are temporary devices configured to mark, and substantially delineate the volume of, surgically created cavities, as well as to function as surgical drains for postoperative drainage of the surgical cavity. That is, the structures described here for marking a cavity and draining fluid are integrated into a single device. Thus, the devices are referred to as fiducial drains. Placing such a device within these cavities, e.g., lumpectomy cavities, may help to provide smaller target volumes for radiation therapy during dose planning, and thus, more accurately target radiation therapy. The temporary nature of the device may be useful given that some patients wish to avoid placement of a permanent or biodegradable implant for tissue cavity marking. These visible, volumetric drainage devices can be placed at the time of surgery into the resection cavity. The mechanism that provides the three dimensional shape of the marking portion can be disengaged or removed percutaneously after radiation therapy has been completed.

The surgical drains described here generally include a tubular conduit having a first drainage lumen and a second member lumen, a proximal portion, a distal portion, and a distal tip, where the second member lumen comprises an inner surface, and a slidably removable shape forming member disposed within the member lumen. The slidably removable shape forming member also has a proximal portion and a distal portion, and may be configured to shape the tubular conduit distal portion. The distal portion of the slidably removable shape forming member may be shaped as a spiral, and may be configured to shape the distal portion of the tubular conduit as a spiral when the shape forming member is disposed within the member lumen of the tubular conduit.

Methods for marking and draining surgical cavities are also described here. These methods generally include the step of placing a resilient, volumetrically shaped distal portion of a fiducial drain device into the surgical cavity, where the device comprises a tubular conduit having a first drainage lumen and a second member lumen, and may include a slidably removable shape forming member, where the slidably removable shape forming member is disposed within the second member lumen, and using the fiducial drain device to aid in identifying a target tissue region for radiation therapy. The fiducial drain may be placed in any suitable surgically created cavity, e.g., a lumpectomy cavity. The methods typically include imaging the cavity region and the fiducial drain, using the position of the fiducial drain to assist with dose planning of the target tissue and adjacent structures, and delivering radiation therapy to the target tissue. After the completion of radiation therapy, the fiducial drain may be removed from the patient by releasing the shape of the distal portion of the device, and then removing the remaining portion of the drain via a standard percutaneous method. This may generally be performed by withdrawing the slidably removable shape forming member from the tubular conduit just prior to final removal of the device from the patient.

BRIEF DESCRIPTION OF THE DRAWINGS

FIG. 1B shows a perspective view of an exemplary distal portion of a slidably removable shape forming member that enables the fiducial drain to be shaped like a Chinese lantern (e.g., having spirals of varying diameter).

In FIG. 2A, the lumen for the shape forming member is incorporated into wall of the tubular conduit. However, the shape forming member may also be housed within a second member lumen that resides freely within the drainage lumen of the tubular conduit, as shown in FIG. 2B.

FIG. 3A illustrates an exemplary method of how the shape of the distal portion of the fiducial drain is released. It shows how the shape forming member may be removed by the clinician.

FIG. 3B shows the shape forming member of FIG. 3A along the recently uncoiled tubular conduit.

DETAILED DESCRIPTION

Figure 1A:
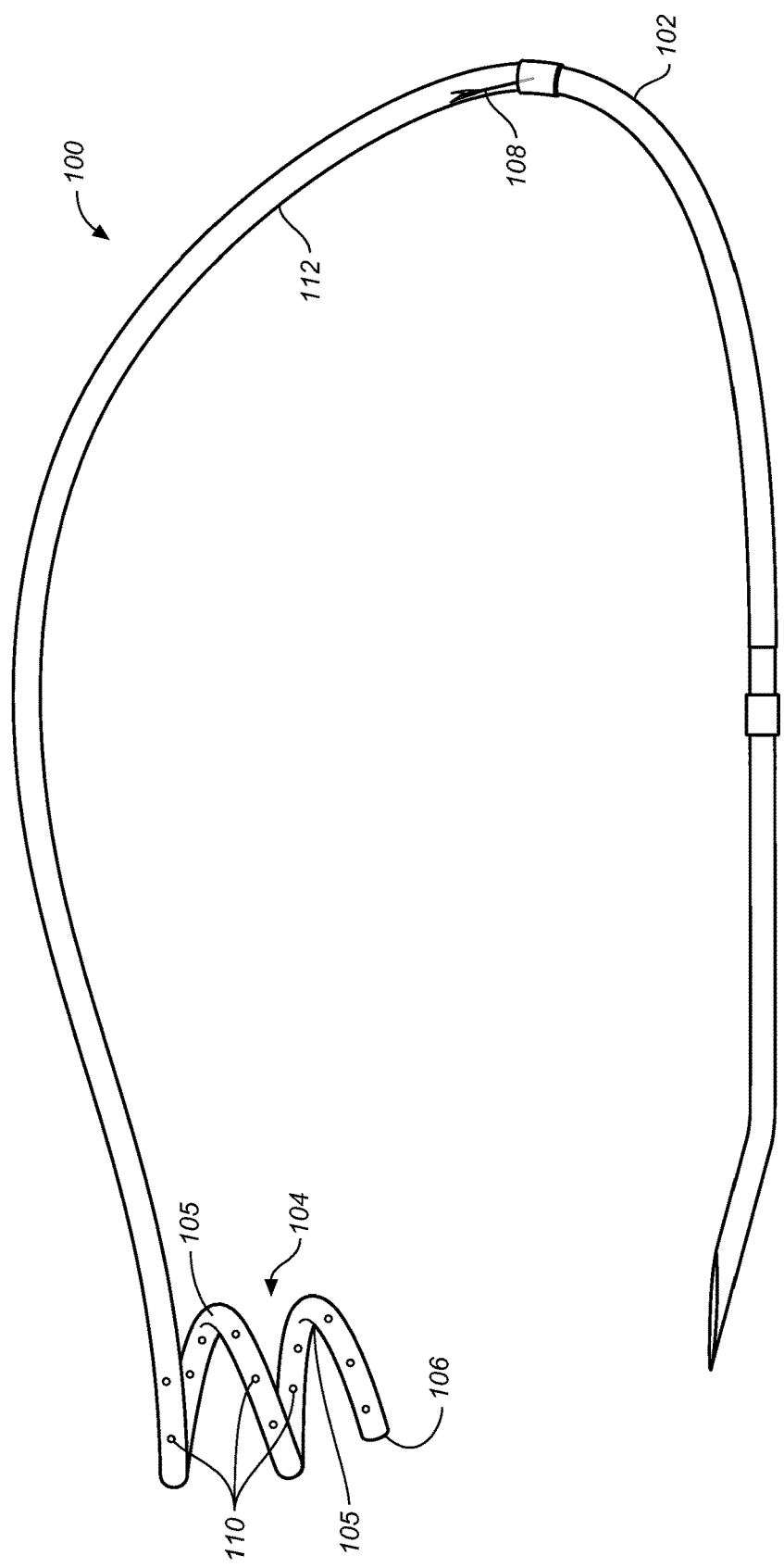
FIG. 1A depicts a perspective view of an exemplary fiducial drain having a spiral-shaped distal portion that has taken its shape from the slidably removable shape forming member (spirals of approximately the same diameter).

Described herein are temporary devices configured to both mark surgically created cavities and drain fluid from the cavities. Placing such a device within these cavities, e.g., lumpectomy cavities, may help to provide smaller target volumes for radiation therapy during dose planning, and thus, more accurately target radiation therapy. The temporary nature of the device may be useful given that some patients wish to avoid placement of a permanent or biodegradable implant for tissue cavity marking.

I. Devices

The fiducial drain devices described herein are generally non-absorbable, and comprise a tubular conduit having a first drainage lumen and a second member lumen, a proximal portion, a distal portion, and a distal tip. The second member lumen usually comprises an inner surface, and a slidably removable shape forming member disposed within it. The slidably removable shape forming member may also have a proximal portion and a distal portion, and may be configured to shape the tubular conduit distal portion. The distal portion of both the tubular conduit and the shape forming member typically reside within the tissue cavity, e.g., resection cavity, lumpectomy cavity, etc.

The tubular conduit is typically flexible enough so that it may conform to the shape of the shape forming member. Flexibility of the tubular conduit may be adjusted by varying the type of material used to make the conduit, by varying wall thickness or diameter of the conduit, etc. The conduit may be made from any suitable polymer material such as silicone, latex, and thermoplastic elastomers. Exemplary thermoplastic elastomers include without limitation, styrenic block copolymers, polyolefin blends, polyurethanes, polyesters, and polyamides. Conduits made from silicone may be particularly useful as they have a long history of being used as drains and offer visibility under x-ray, particularly if enhanced with a co-extruded radiopaque stripe or with a radiopacity-enhanced formulation (e.g., silicone compounded with barium sulfate). The wall thickness of the conduits may range from between about 1 mm to about 3 mm.

As previously stated, the tubular conduit may have a first drainage lumen for draining fluid out of the cavity, and a second member lumen within which the slidably removable shape forming member is disposed. In some variations, the tubular conduit may include a liner within either the drainage lumen or the second member lumen to facilitate low friction removal of the shape forming member that is disposed within the liner. The drainage lumen may extend from the distal tip through the proximal portion of the conduit, and have a diameter ranging from about 3 mm to about 4 mm. The member lumen may have various configurations and will generally have a smaller diameter than the drainage lumen, e.g., an outer diameter of about 1-2 mm, but not always. In one instance, the member lumen is formed within the wall of the tubular conduit. In other variations, the member lumen may be an eccentrically disposed lumen within the drainage lumen. In yet a further variation, the member lumen may be a lumen that is concentrically placed within the drainage lumen. The tubular conduit in some variations is a double lumen catheter, where one lumen is the first drainage lumen, and the other lumen is the second member lumen. The member lumen (or liner) may be fabricated from polymer tubing having low friction properties, to reduce friction when the slidably removable shape forming member is withdrawn from the member lumen. Such materials may include fluorinated ethylene propylene (FEP), polytetrafluoroethylene (PTFE), or high durometer plastics such as polyimide or polyether ether ketone (PEEK). Some variations of the member lumen (liner) may comprise portions of varying durometer (hardness), e.g., at least two portions of different durometer in their cross-section or along their length. For example, a higher durometer material (or thicker walled region) along the length portion of the member lumen near the skin surface may allow for less deformation of the drain at the skin region as the shape forming member is removed. This feature may therefore be more comfortable for the patient during member lumen removal.

In addition, lubricious materials such as hydrophilic coatings or lubricants may also be provided on the surface of the member lumen. For example, it would be beneficial to have the inner surface of the spiral-shaped portion of the lumen coated with a lubricious polymer.

To facilitate fluid drainage in the postoperative period, and to facilitate conduit flexibility, the tubular conduit may include a plurality of apertures axially spaced along any portion of its length. The apertures may be of any suitable size and shape, e.g., circular, square, etc. The apertures may also be spaced any suitable distance from each other. For example, they may be spaced about 0.5 cm to about 1 cm apart. The apertures may further be spaced symmetrically or asymmetrically along the length of the conduit, and may be positioned along the portion of the drain tubing (conduit) that resides within the patient. In some variations, the tubular conduit includes depth markings on its outer surface to help identify the position of the drain within the patient. After placement of the fiducial drain into the cavity, the proximal portion of the drain is driven through the skin of the patient via a trocar so that the proximal portion of the conduit resides external to the patient. The trocar may be subsequently cut from the device, and the remaining proximal end of the conduit may be connected to a source of vacuum, e.g., a Jackson-Pratt bulb reservoir.

The shape forming member may be a wire, e.g., a metallic wire or a high durometer plastic filament. Exemplary materials for the metallic wire include without limitation, cobalt, chromium, Iron, Molybdenum, Manganese, Nickel, stainless steel (including tempered stainless steel), Titanium, other resilient metals, and alloys thereof. Elgiloy® metal alloy may be employed. Wires made from superelastic Nickel-Titanium alloy may be particularly useful. Some variations of the wires, e.g., the superelastic Nickel-Titanium alloy wires, may have a diameter ranging from about 0.02 inch (20 mil) to about 0.035 inch (35 mil). As previously stated, the shape forming member may reside within the member lumen, and may include a proximal portion and a distal portion. The distal portion of the shape forming member may have any suitable size, shape, or geometry that allows a three dimensional volume or region to be marked and imaged as it resides within or along the drainage lumen. It is understood that the shaped distal portion of the fiducial drain should be resilient and resist collapse of the coils while implanted (e.g., during movement of the patient and/or adjacent tissue). In one variation, the distal portion of the shape forming member is shaped like a spiral. Here the diameter of the coils of the spiral may be the same or different. The diameter of the coils may range, e.g., from about 2 cm to about 5 cm in length. The coils may also be spaced from each other any suitable distance, e.g., from about 0.5 cm to about 2 cm. Alternatively, the distal portion of the slidably removable shape forming member may be shaped to resemble a Chinese lantern, i.e., having spirals with smaller diameters at the ends, and larger diameters in the middle section. As previously stated, the shape of the shape forming member generally shapes the distal portion of the tubular conduit when the shape forming member is disposed within the member lumen of the conduit. In some variations, the proximal end of the shape forming member is textured or enlarged in diameter (e.g., via a welded ball) to improve grip on the member when withdrawing it from the member lumen.

At least the distal portion of the tubular conduit (the portion within the cavity) may be radiopaque. The radiopaque properties may be inherent to the conduit itself (e.g., silicone with or without an additional barium sulfate formulation), or may be provided by radiopaque markers (e.g., titanium clips or gold markers) located at various positions along the distal portion of the conduit, on the conduit surface, or within its walls, or by coating or impregnating the conduit with a radiopaque material. The shape forming wire may also add to the radiovisibility of the device under x-ray, CT, MRI, or ultrasound. Some variations of the device may also have a tubular conduit that is enhanced with an antibiotic or infection-mitigating agent (e.g., silver compounds, or antibiotics such as minocycline and rifampin). For example, the antibiotic or infection-mitigating agent may be coated on, or impregnated within the material of, at least a portion of the tubular conduit. The distal tip of the tubular conduit may also be formed to be open or closed ended. When open, the opening will generally communicate with the first drainage lumen. If closed, closure of the conduit may be provided by placing a blunt structure, such as a nose cone at the distal tip (e.g., a molded silicone nose cone may be bonded to the drain at the distal tip). A mechanism for temporarily housing the proximal end of the shape forming member within the device (e.g., during device placement) may also be provided in the tubular conduit. For example, a slit or channel may be placed in the wall of a region of the conduit that resides outside the patient. With this construction, the shape forming member may be lifted out from the slit or channel so that the clinician can grab the proximal end of the member to withdraw it from the remainder of the drain, typically just prior to removal. The slit or channel may be covered by a slidable ring or band until needed. A slidable ring or band may also be used to secure the proximal end of the shape forming member to the tubular conduit.

An exemplary fiducial drain is shown in FIG. 1A. Referring to the figure, fiducial drain (100) may comprise a tubular conduit (112) having a proximal portion (102), a distal portion (104), and a distal tip (106). A slidably removable shape forming member (108) resides within (this aspect not shown), and extends from, a member lumen (not shown). Apertures (110) are axially spaced along a portion of the length of the tubular conduit. Although the distal portion (104) is shaped as a spiral having coils (105) of approximately the same diameter, it may also be shaped to resemble a Chinese lantern (114), as shown by the alternate shape forming member in FIG. 1B. With the Chinese lantern (114) shape, proximal and distal coils (118, 120) have a smaller diameter than coils (116) in the mid-section.

Figure 2A:
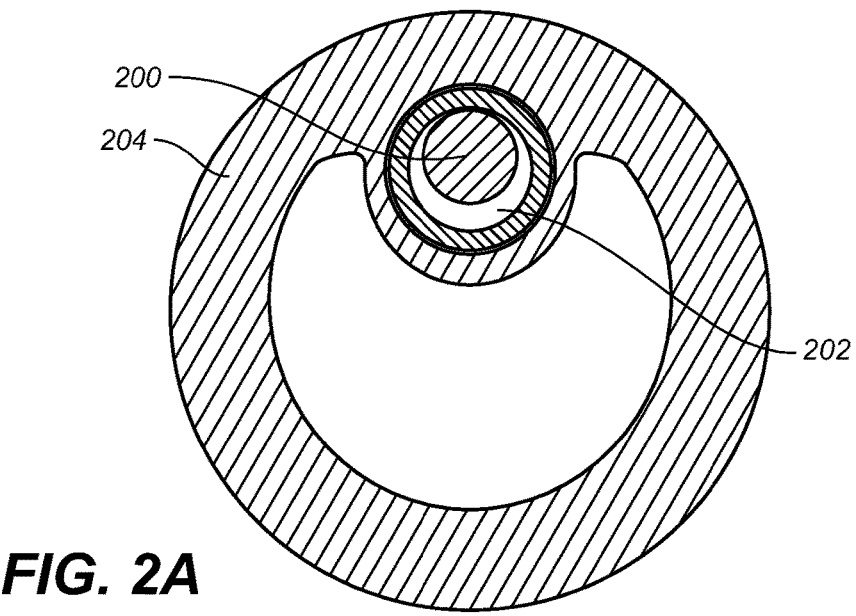
FIG. 2A depicts a cross-sectional view of the fiducial drain of the type described in FIG. 1A.
Figure 2B:
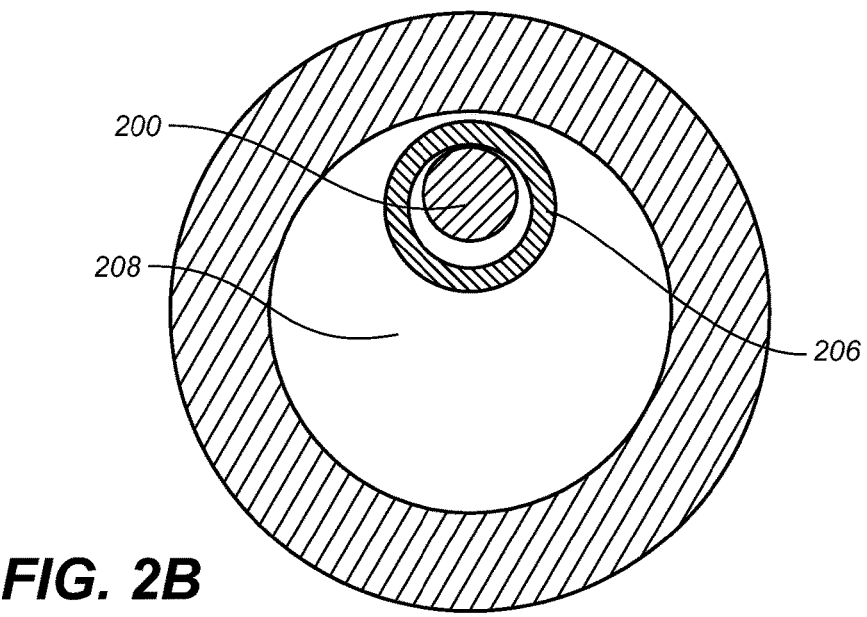

The second member lumen of the fiducial drain devices may have any suitable configuration that allows, e.g., the tubular conduit to conform to the shape of the shape forming member, and allows the shape forming member to be withdrawn from the member lumen relatively easily. In some variations, and as shown in FIG. 2A, the shape forming member (200) may be disposed within a tubing segment or lumen (202) formed within the wall (204) of the tubular conduit. In other variations, the member lumen may be a separate tubing segment (206) within the drainage lumen (208) of the tubular conduit.

Although the fiducial drains may be formed as a unitary device, some variations may include two or more separate components that can be put together at the time of surgery. For example, the distal shaped portion of the drain may be snap fit onto the distal end of a tubular conduit. A typical snap fit would be a press fit male and female tubular fitting. Various sizes of the spiral end may be provided, e.g., in a kit, so that the surgeon may choose and properly size the coil of the fiducial drain to match the size of the surgical resection cavity.

In summary, some of the useful features of the fiducial drains described herein include: 1) that they provide temporary, nonabsorbable targets for radiation therapy having an integral, post-surgical wound drainage system; 2) they help to more accurately visualize the target volume to be subjected to radiation therapy; 3) they are able to define a three-dimensional volume or region; 4) they can be placed (in the cavity) at the time of surgery; 5) they are capable of collapsing or changing/releasing their shape to facilitate removal from the cavity; and 6) they include at least two lumens, one for housing a shape forming member (that can also release the shape upon removal from the drain), and one for drainage of fluid.

II. Methods

Various methods of using the fiducial drains are also described here. These methods generally include the step of selecting a properly sized fiducial drain device, and placing a shaped distal portion of a fiducial drain device into the surgical cavity, where the device comprises a tubular conduit having a first drainage lumen and a second member lumen, and may include a slidably removable shape forming member, where the slidably removable shape forming member is disposed within the second member lumen. The fiducial drain may be placed in any suitable surgically created cavity, e.g., a lumpectomy cavity, using the standard technique for inserting surgical drains. The methods may further include imaging the cavity and the fiducial drain, dose planning, and delivering radiation therapy to the cavity region and/or target tissue. The target tissue may generally be the region of tissue delineated or otherwise identified with the aid of the fiducial drain. The fiducial drain may aid in identifying the target tissue by draining seroma from the surgical cavity and reducing the size of the seroma cavity. The fiducial drain may also aid in identifying the target tissue by visualizing elements of the drain that are visible during radiation planning or therapy via CT or other forms of clinical imaging (e.g. X-ray, MRI, ultrasound). Some of the radiation methods and regimens that may be employed include three-dimensional conformal external beam radiation, IMRT (intensity-modulated radiation therapy), IGRT (image-guided radiation therapy), and VMAT (volumetric arc therapy), stereotactic radiotherapy, and electron boost. For example, the fiducial drain may be imaged to help position the patient using IGRT techniques in the delivery of their dose fraction of radiation therapy. The radiation therapy may be delivered in an accelerated or a conventional dose fractionation scheme.

After the completion of radiation therapy, the methods described here may include removing the fiducial drain from the surgical cavity. To remove the fiducial drain, the drain must generally change from (i.e., be released from) a first, shaped configuration, to a second, more easily straightened, slidably removable configuration. For example, and as illustrated in FIG. 3A, the fiducial drain may be removed from the patient by releasing the shape of the distal portion of the device. The proximal portion (300) of the drain lies outside the cavity. This may generally be performed by pulling on the distal end (302) of the shape forming wire that is outside the cavity in the proximal direction (direction of arrow 1) to collapse or straighten the shape (e.g., a spiral), and withdrawing the slidably removable shape forming member from the tubular conduit. Once removed (as shown in FIG. 3B), the distal portion (304) of the drain may be removed from the cavity since the spiral shape induced by the shape forming member (306) has been effectively eliminated.

More specifically, and with respect to the treatment of breast cancer, when the patient goes to CT for radiation therapy planning, the spiral silicone tubing and the reinforcing wire (shape forming member) of the drain are visible radiographically (e.g., by CT), in a manner that guides the radiation oncologist on the location of the lumpectomy cavity and/or area to be treated. After radiation therapy is administered (e.g., in an accelerated 10 day regimen), the drain may be removed.

The invention claimed is:

1. A method for marking and draining a resection cavity comprising:
   placing a resilient, spiral shaped distal portion of a fiducial drain device into the resection cavity, the fiducial drain device comprising a tubular conduit having a first drainage lumen and a second member lumen, and a slidably removable shape forming member, wherein the slidably removable shape forming member is disposed within the second member lumen during drainage of fluid from the resection cavity and comprises a spiral shaped distal portion having a plurality of coils;
   using the plurality of coils to delineate the volume of the resection cavity and aid in the identification of a target tissue of the resection cavity for delivery of external beam radiation therapy;
   delivering external beam radiation therapy to the target tissue while the slidably removable shape forming member is disposed within the second member lumen; and
   removing the fiducial drain device from the resection cavity by withdrawing the slidably removable shape forming member from the second member lumen to release the spiral shape of the fiducial drain device distal portion.

2. The method of claim 1, wherein the slidably removable shape forming member comprises a wire.

3. The method of claim 2, wherein the wire comprises Nickel, stainless steel, Titanium, or alloys thereof.

4. The method of claim 3, wherein the wire comprises a superelastic Nickel-Titanium alloy.

5. The method of claim 1, wherein the resection cavity is a lumpectomy cavity.

6. The method of claim 1, further comprising imaging the resection cavity and the fiducial drain.

7. The method of claim 6, further comprising creating a dose plan based on the imaging.

* * * * *